United States Patent [19]

Hurwitz

[11] 4,252,024

[45] Feb. 24, 1981

[54] FLAW DETECTION, CHARACTERIZATION AND STUDY

[75] Inventor: Michael J. Hurwitz, Pittsburgh, Pa.

[73] Assignee: Westinghouse Electric Corp., Pittsburgh, Pa.

[21] Appl. No.: 961,788

[22] Filed: Nov. 17, 1978

[51] Int. Cl.² ............................................. G01N 29/04
[52] U.S. Cl. ........................................ 73/603; 73/607; 73/626; 367/8
[58] Field of Search ............... 73/603, 606, 607, 618, 73/620, 625, 626, 627, 633; 340/5 MP, 5 H, 3 R; 128/660

[56]   References Cited
        U.S. PATENT DOCUMENTS 3,721,312   3/1973   St. John ............................... 73/603
4,021,771   5/1977   Collins et al. ....................... 340/5 H Primary Examiner—Stephen A. Kreitman
Attorney, Agent, or Firm—D. C. Abeles

[57] ABSTRACT

Echo ranging flaw detecting, characterizing and studying apparatus in which the work is scanned simultaneously by acoustic energy focused at a point from an acoustic-lens transducer and by acoustic energy focused along a line along which it is propagated from a focused-arc transducer. The acoustical echos from the lens transducer are combined with an electrical analog of an acoustical reference wave to produce an acoustical interference pattern which is reconstructed into a holographic display or hologram by a laser beam. The echos from the focused-arc transducer produce a cathode-ray tube display or are stored in a memory.

8 Claims, 11 Drawing Figures

FLAW DETECTION, CHARACTERIZATION AND STUDY

REFERENCE TO RELATED DOCUMENTS

This application relates to and incorporates by reference an application Ser. No. 961,787, filed concurrently herewith to Michael J. Hurwitz for "Detection, Characterization And Studying Of Flaws In Work By Acoustic Imaging" and assigned to Westinghouse Electric Corporation (herein called Hurwitz application).

BACKGROUND OF THE INVENTION

This invention relates to detection, characterization and study of flaws, and has particular relationship to flaw detection by echo ranging of acoustic energy and by holographic processing. Acoustic flaw detection is uniquely useful for the detection of flaws in metal. It has found extensive applicability in the detection of flaws in pressure vessels of nuclear reactors. For this purpose a high-resolution ultrasonic imaging system has been developed for defining the dimensions and orientation of the flaws. In flaw detection acoustic energy scans the work or the specimen subject to flaw inspection.

In one mode of sonic or acoustic imaging, acoustic energy is focused at points of the scanning pattern on or near the surface. With the acoustic energy so focused the area under observation is all, of a part, of the surface of the work on which this acoustic energy impinges, or any plane parallel to this surface within the work. The acoustic energy impinging on the work at each point produces a broad beam pattern diverging from the point. A C-scan image is derived from this mode of scanning. A C-scan image is an image of the surface, or of any plane within the work perpendicular to the direction of propagation of the scanning acousting energy. A flaw constitutes a discontinuity in the work and a wave of the expanding beam which encounters such a discontinuity is reflected as an echo. A display of the echo pattern is produced from the response of a sensor to the echos. Typically, the acoustical echo pattern may be mixed with an electrical analog of an acoustical reference wave to produce an acoustical interference pattern, i.e., a hologram. The hologram may be reconstructed by a laser beam into a recognizable optical image.

In another mode of acoustic imaging the acoustic energy is focused along a line which scans the work and at each point is propagated into the work. The imaging produced with such scanning is referred to as line-focused imaging. The acoustic energy impinging on a flaw at any point along the line is reflected as an echo. Such a scan may produce a series of what is referred to as B-scan acoustic images. A B-scan is a scan in a plane parallel to the direction of propagation of the acoustic energy. The definition of line-focused images is comparable to that produced holographically as described above. The images derived from the line-focused energy may be displayed on a cathode ray oscilloscope or may be stored in a memory for later display. The line-focused acoustical energy may also be used to produce a C-scan image by selecting echo intelligence received only from a predetermined depth in the work.

SUMMARY OF THE INVENTION

In accordance with this invention acoustic apparatus for flaw detection, characterization and studying is provided in which different modes of acoustic imaging and their different displays are integrated. Specifically, point-focused imaging, in which the scanning is by acoustic energy focused on or near the surface of the work and the display is a hologram, is integrated with line-focused imaging, in which the scanning is by acoustic energy focused along a line and the display is on a cathode-ray oscilloscope. Work-scanning means common to the point-focused acoustic energy and to the line-focused acoustic energy is provided. The integration is effected by sharing the scanning cycles, alloting a part of the scanning cycle exclusively to point-focused energy and another part to line-focused energy. The receipt and processing of intelligence from line-focused propagation is suppressed, responsive to the position of the scanning mechanism, during the part of the scanning cycle alloted to point-focused propagation and the receipt and propagation of intelligence from point-focused propagation is suppressed during the other part of the cycle. The modes of propagation and their corresponding imaging dovetail into each other. The acoustic energy propagated and the displays are coordinated, each mode of propagation and display complementing the other so that the positions and forms of the flaws can be determined with precision.

BRIEF DESCRIPTION OF THE DRAWINGS

For a better understanding of this invention, both as to its organization and as to its method of operation, together with additional objects and advantages thereof, reference is made to the following description taken in connection with the accompanying drawings, in which.

Figure 1:
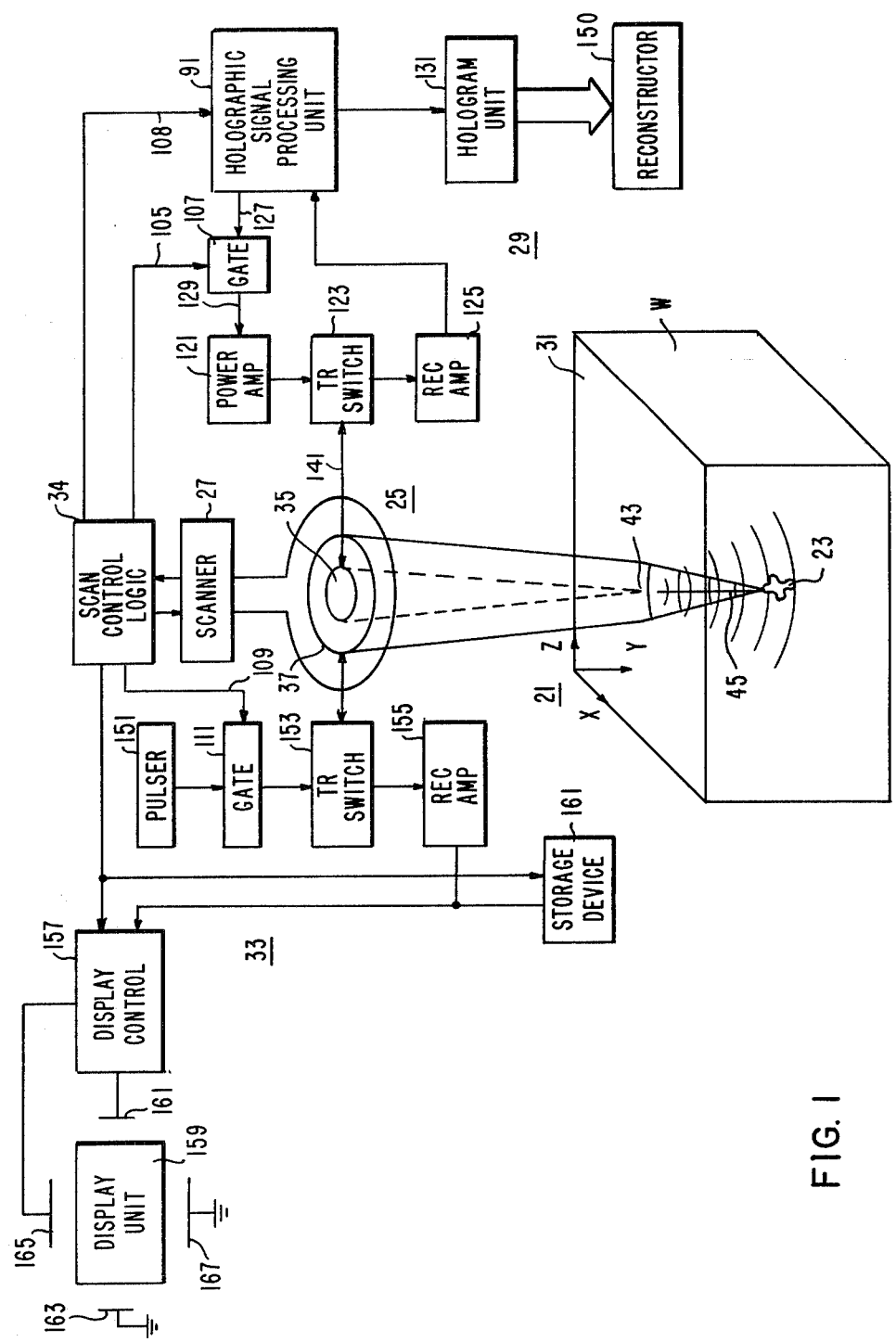
FIG. 1 is a block diagram showing an embodiment of this invention.
Figure 2:
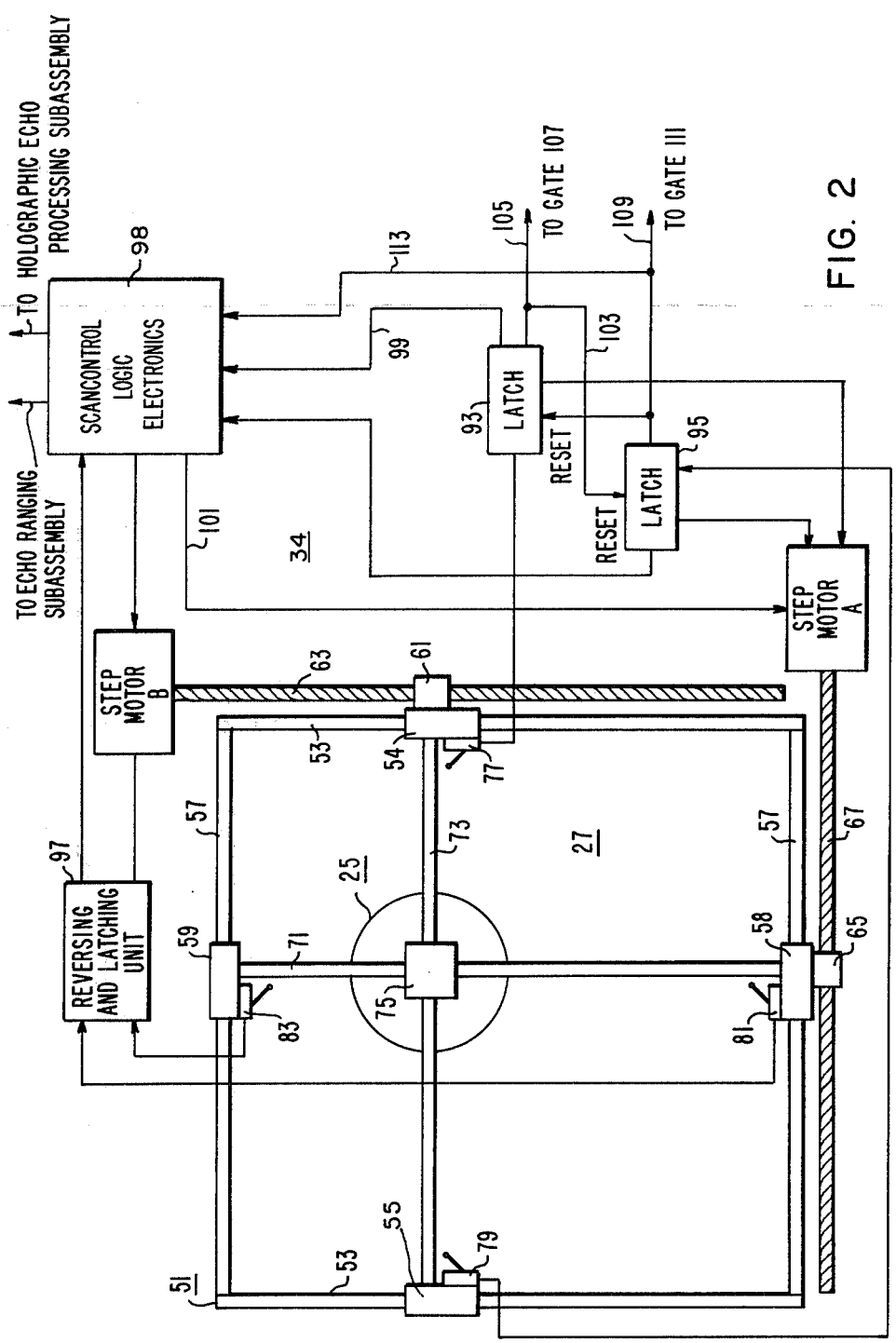
FIG. 2 is a plan view, partly diagrammatic, showing the scanning mechanism used in the practice of this invention which integrates the different modes of imaging in the practice of this invention.
Figure 7:
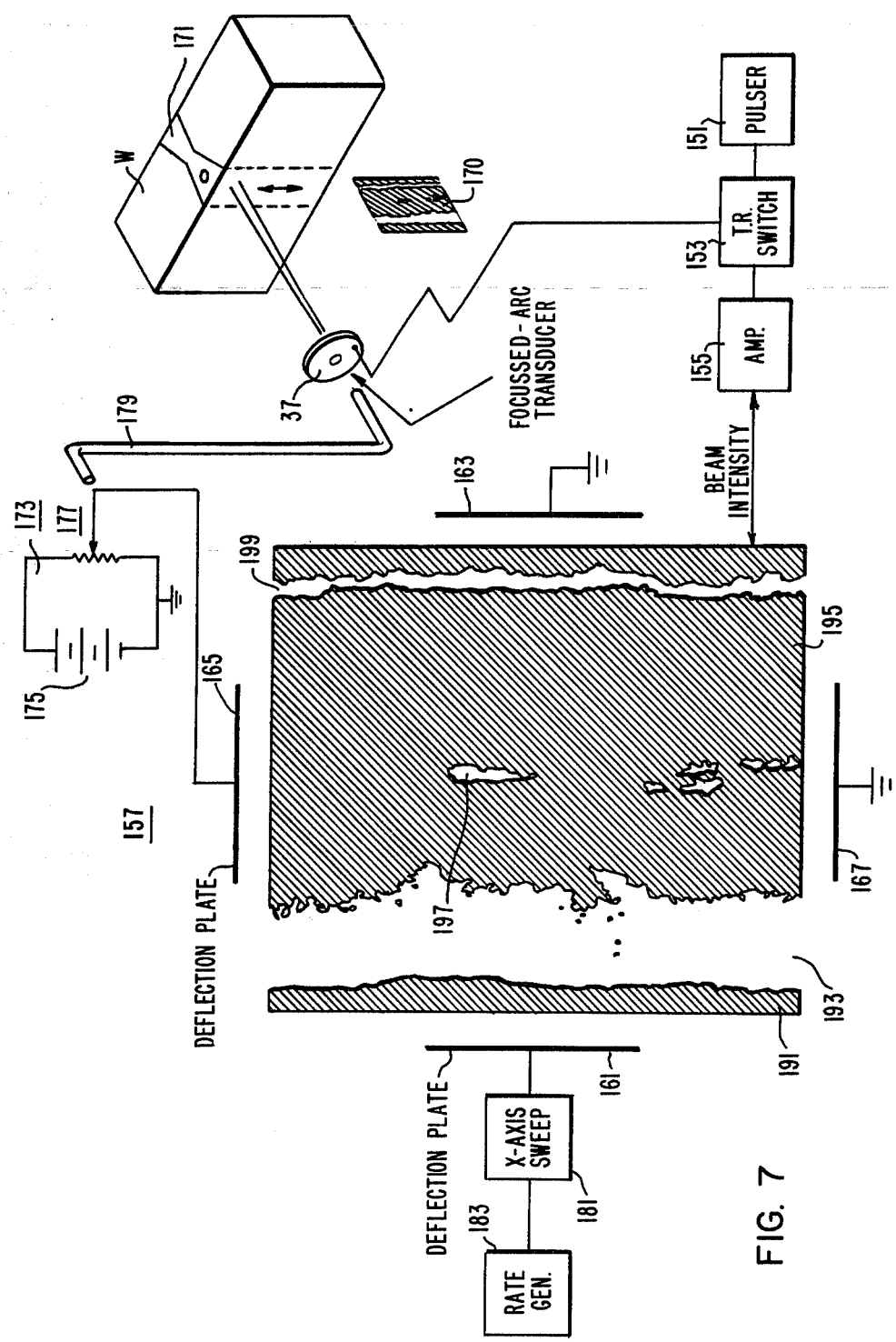
FIG. 7 is a diagram illustrating the operation of a focused-arc transducer in producing a B-scan.

The blocks of the block diagrams of FIGS. 1, 2 and 7 on the whole correspond to functions of the apparatus in accordance with this invention rather than structurally separate components. The functions are derived from an integrated structure, either solid state logic or a computer, which may not be physically divisible in accordance with the blocks of the block diagrams.

DETAILED DESCRIPTION OF THE EMBODIMENT

FIGS. 1 through 6 show flaw detection apparatus 21 for detecting flaws 23 in the work W. The work W is in the form of a rectangular parallelepiped. For the sake of convenience in describing this invention, the surfaces of the work are referred to as a three-dimensional coordinate system whose X and Z axes are along the sides of the upper surface 31 and whose Y axis is along the edges perpendicular to this surface, i.e, along the depth of the work W. A C-scan acoustic image is the image produced by scanning the X–Z coordinate plane surface or any surface parallel to it. A B-scan acoustic image is the image produced by scanning in depth parallel to the X–Y or Y–Z coordinate plane.

The flaw detection apparatus 21 includes a transducer subassembly 25. This subassembly is driven by scanner 27 to scan the work W. The apparatus also includes a holographic echo-processing subassembly 29 for the holographic mode of acoustic imaging and an echo-ranging subassembly 33 for the line-focused mode of imaging in which the acoustic energy is focused along a line perpendicular to surface 31. The scanner is driven and its scanning is coordinated with the operation of the holographic echo-processing subassembly 29 and of the echo ranging subassembly by scan control logic 34 (FIGS. 1 and 2). The work W is immersed in water, and the transducer subassembly 25 extends into the water propagating the acoustic energy to the work through the water.

The transducer subassembly 25 includes a point-focussing transducer which typically may be a conventional acoustic-lens transdcuer 35 and a focused-arc transducer 37. In lieu of an acoustic-lens transducer, the point-focussing transducer may be a transducer provided with a reflector for concentrating the acoustic energy at a point or a concave-shaped transducer formed to concentrate the energy at a point or a focussing array of small transducers. The acoustic-lens transducer 35 produces a beam of acoustic energy which is focused on or near the surface 31 of the work. A broad beam pattern diverges from the focal point penetrating into the work. Flaws in the work reflect echoes which are propagated to the transducer 35 (or to a separate receiver-transducer) and processed. Typically, the frequency of the acoustic energy propagated by transducer 35 is 1 to 5 megahertz.

Figure 5:
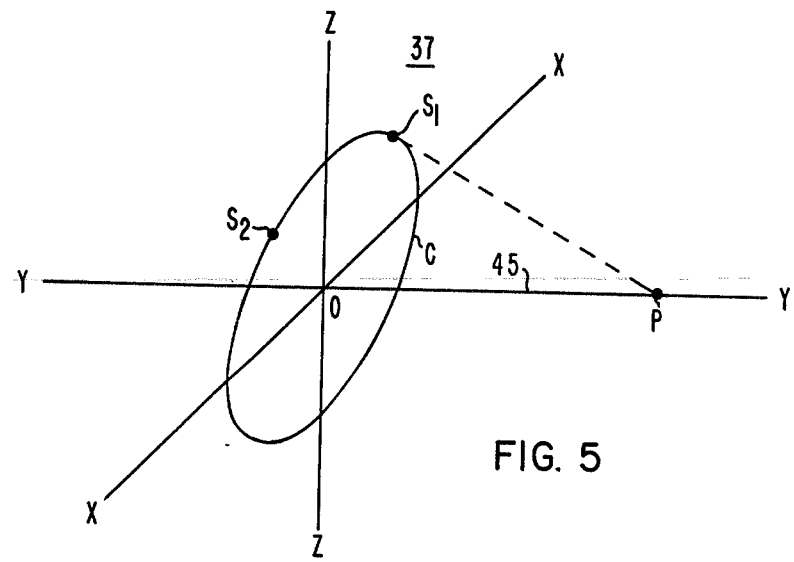
FIG. 5 is a diagram illustrating the manner in which the focused-arc transducer used in the line-focused propagation operate in the practice of this invention.

The operation of the focused-arc transducer 37 may be understood from a consideration of FIG. 5. The three-dimensional coordinate axes X, Y, Z shown in FIG. 5 and the planes which they define are assumed to be parallel to the axes X, Y, Z along the edges of the work W in FIG. 1 and to the planes including the surfaces of the work which these latter axes define. Assume that there are a plurality of acoustic sensors $S_1$, $S_2$, etc. along a circle or ring C in a plane X–Z whose center is at 0. These sensors $S_1$, $S_2$, etc. may extend over the whole circumference of circle or ring C or over any arc or arcs of the circumference. If these sensors $S_1$, $S_2$, etc. are excited acoustically, they radiate acoustic energy in all directions. If the excitation of $S_1$, $S_2$, etc. is such that they radiate in phase, the energy arriving at any point P along the Y axes from all sensors is in phase since the distances L from all points of the circumference of the circle C to any point P are equal. The acoustic waves arriving at point P from the sensors $S_1$, $S_2$, etc. reinforce each other. The acoustic energy from sensors $S_1$, $S_2$, etc. is focused at all points along the Y axis. Conversely, sound transmitted, or an echo reflected, from any point P along the Y axis will arrive and activate receiving sensors disposed along circle C in phase. The signals received by all these sensors reinforce each other and these signals are added so that a strong total signal is provided.

The time of arrival from any point P along axis Y is proportional to the distance of the point P from the points $S_1$, $S_2$, etc. Where the point P is displaced a long distance from the ring C, this time of arrival is, to a close approximation, proportional to the distance P0. The acoustic energy from the sensors $S_1$, $S_2$, etc. arrives at different phases at points not along axis Y and there is no mutual reinforcement. This acoustic energy is then of substantially smaller magnitude than that along axis Y. Conversely, an echo from a point not along axis Y arrives at sensors along circle or ring C in different phases and the received signal derived by adding the individual signals received by the sensors is substantially weaker than a signal from an echo along axis Y.

The focused-arc transducer 37 includes a plurality of sensors 41 (FIGS. 3, 4) disposed in a circular array or ring. This circular array may be concentric with the acoustic-lens transducer 35; the circular array (41) may also be eccentric with respect to the acoustic-lens transducer; i.e., the axis of the acoustic-lens transducer may be displaced radially from the axis of the circular array. The concentric arrangement has the advantage that, at any instant, the focused-arc transducer and the acoustic-lens transducer cover the same scanned area. The acoustic-lens transducer 35 and the sensors 41 along the circular array operate both to transmit the acoustic energy and to receive the echoes. The acoustic energy from the acoustic-lens transducer 35 is focused at a point 43 at or near the surface 31. The acoustic energy from the focused-arc transducer 37 is focused along a line 45, extending along the depth of the work W and perpendicular to the surface 31. At each point of surface 31 to which the acoustic energy is propagated, the acoustic energy is focused progressively along the corresponding line 45. The rate at which the surface is scanned is typically low compared to the rate at which the acoustic energy moves along line 45 so that the movement of the focus may be regarded as taking place along a line perpendicular to surface 31 rather than along a line at an appreciable angle to surface 31. A flaw 23 encountered by acoustic energy propagated along line 45 produces an echo which is reflected back to the transducer 37 and is processed. Typically the acoustic energy transmitted and received by the focused-arc transducer has a frequency of 1 to 5 megahertz.

Different sensors of the focused-arc transducer may serve for transmitting and receiving. For example, sensors in one quadrant may serve for transmitting and sensors in another quadrant may serve for receiving. Alternatively, coaxial rings or circular arrays of sensors may be provided, the sensors of one ring for transmitting and the sensors of another ring for receiving.

The scanner 27 (FIG. 2) includes a rectangular frame 51. One pair of opposite members 53 forming the frame 51 serves as tracks or guides for the bearings 54 and 55 which are moved to produce scanning of the work W along one dimension. The opposite members 57 forming the frame serve as tracks or guides for the bearings 58 and 59 which are moved to produce the scanning in the perpendicular dimensions. The bearing 54 carries a nut 61 which meshes with a screw 63 driven by step motor B. The bearing 58 carries a nut 65 which meshes with a screw 67 driven by step motor A.

Figure 3:
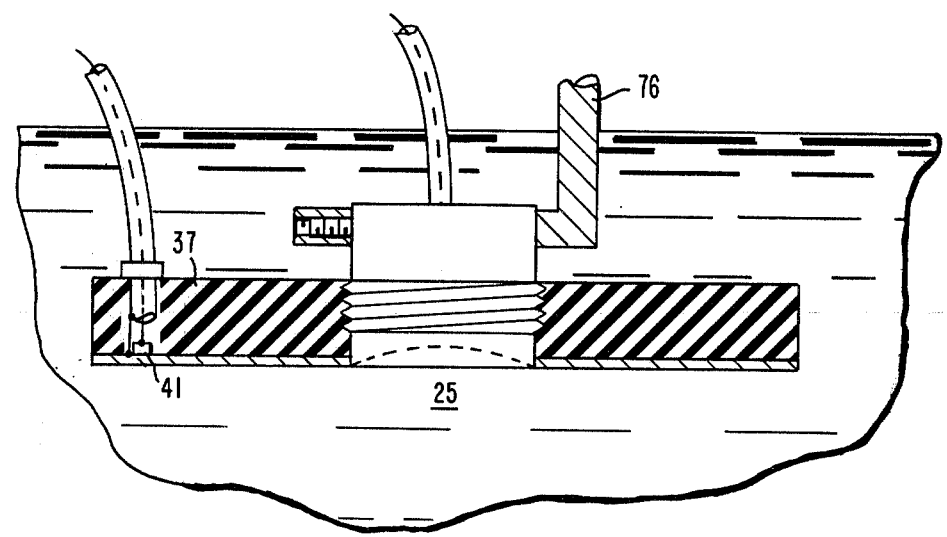
FIG. 3 is a view in side elevation showing the transducer subassembly of the embodiment shown in FIG. 1 and the manner in which the subassembly is suspended.
Figure 4:
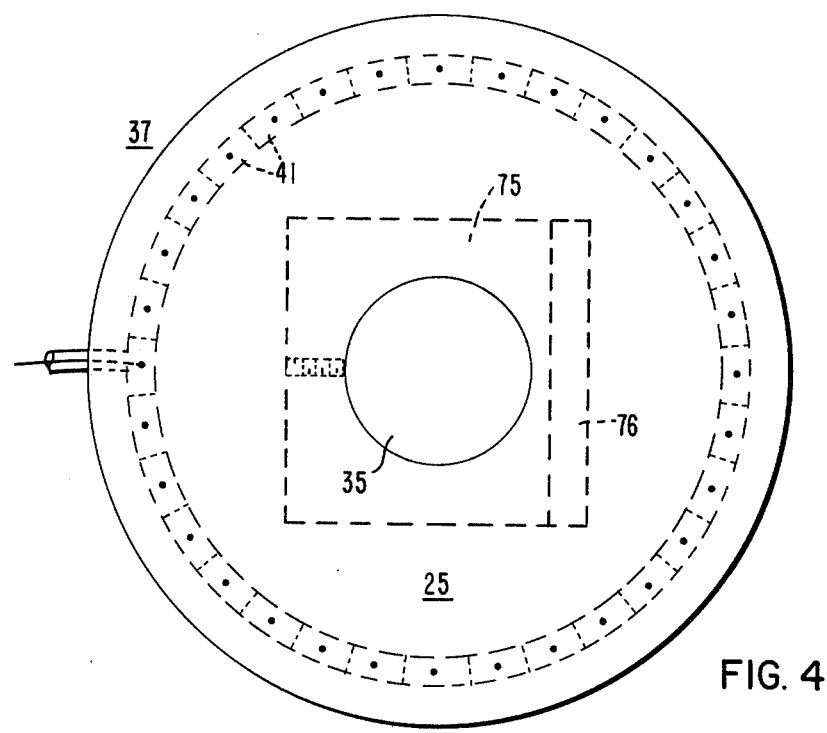
FIG. 4 is a plan view of the transducer assembly shown in FIG. 1.

The bearings 54 and 55 support a cross bar 73 and the bearings 58 and 59 support a cross bar 71. Cross bar 71 is below cross bar 73. Cross bars 71 and 73 serve as guides or tracks for a block 75 which engages the bars 71 and 73 and from which the transducer subassembly 25 is suspended by a suspension bar 76 (FIG. 3). Bearings 54 and 55 each carry a limit switch 77 and 79 and bearings 58 and 59 each carry a limit switch 81 and 83. Rotation of screw 63 by motor A advances bearings 54, 55, bar 73 and block 75 and transducer subassembly 25 vertically as viewed in FIG. 2 in one direction or the other. When the block 75 reaches its lower limit, it actuates switch 81; when it reaches the upper limit, it actuates switch 83. Rotation of screw 67 advances bearings 58, 59, bar 71, block 75 and transducer subassembly 25 to the right or left as viewed in FIG. 2. When block 75 reaches the right-hand limit, it actuates switch 77, and when it reaches the left-hand limit it actuates switch 79.

The scan-control logic 34 (FIG. 2) includes latches 93 and 95, reversing and latching unit 97 for motor A and motor B and scan-control logic electronics 98. The scan-control logic electronics 98 supplies driving pulses for the motors A and B and, by cooperation with latches 93 and 95, the holographic echo-processing subassembly 29 and the echo ranging subassembly 33 coordinates the scanning and the processing of signals during separate parts of the scanning cycle by the subassembly 29 and the subassembly 33. The scan-control logic electronics 98, through conductor 108 (FIG. 1), also provides the intelligence for the phase adjustment of the electrical analog of the acoustical reference wave for the holographic echo-processing subassembly. The wave itself is derived from an oscillator in the holographic signal processing unit 91 which also includes the transmit power amplifier.

The impressing of the pulses on motors A and B and their polarity is controlled by the electronic latches 93 and 95. The latches 93 and 95 are actuated and locked in their actuated setting on actuation of the limit switches 77 and 79. The limit switches are actuated by the block 75 at the end of each horizontal sweep as viewed in FIG. 2. The latching unit operates on actuation of limit switches 81 and 83 at the ends of vertical sweeps.

In operation of the scanner 27 it may be assumed that the block 75 is at the top of frame 51 where it has actuated the limit switch 83. The reversing and latching unit 97 then has sent a signal to the scan-control logic electronics 98 to prevent the motor B from driving the block 75 upwardly and to enable motor B to drive the block 75 downwardly as viewed in FIG. 2. Also assume that the block 75 is at the right-hand end of its sweep. Latch 93 has been actuated by actuation of switch 77. Latch 93 has, through connection 99, disabled the scan-control logic electronics 98 from stepping motor A through connection 101, to drive the block 75 to the right and has enabled the electronics 98 to step motor A so that block 75 moves to the left. Through conductor 103 latch 93 resets latch 95. In addition, latch 93 enables the scan control logic electronics 98, through conductor 105, to set gate 107 of the holographic echo-processing subassembly 29 to block the transmission of acoustic energy to the acoustic-lens transducer 35 or the processing by subassembly 29 of echoes resulting from the transmissions of focused-arc transducer 37. Latch 95 when enabled has enabled the electronics 98, through conductor 109, to set gate 111 of the echo-ranging subassembly 33 to permit the transmission of electrical pulses to the focused-arc transducer 37 and the processing of the echoes from these pulses.

The scan-control logic electronics 98 now supplies pulses to motor A to move the block 75 and the transducer subassembly 25 to the left. Because gate 111 is open, the acoustic energy is transmitted to, and received by, the echo-ranging subassembly 33 while the holographic echo-processing subassembly 29 is dormant because gate 107 is closed.

When block 75 reaches the end of its left-hand sweep, limit switch 79 is actuated, actuating latch 95. Gate 111 is now blocked, suppressing transmission of acoustic energy to or reception of echoes from the focused-arc transducer. The electronics 98 is set through conductor 113 to discontinue the stepping of motor A so that block 75 moves to the left and to enable the stepping of this motor so that block 75 moves to the right. In addition, latch 93 causes electronics 98 to open gate 107 so that acoustic energy is transmitted to, and echoes are received from, the acoustic-lens transducer 35. At this stage, motor B is actuated to move block 75 one increment downwardly as viewed in FIG. 2.

The block 75 and transducer assembly 25 now are moved to the right. When the block 75 reaches the end of the sweep to the right, limit switch 77 is actuated. Latch 93 now repeats the above-described operations and in addition electronics 98 is actuated to step motor B so that the block 75 is moved another increment downwardly. The movement of block 75 to the right and to the left is repeated. The above-described operation continues until block 75 actuates switch 81. At this point the reversing and latching unit 97 is actuated to prevent downward stepping and step motor B is stepped to reset the block 75 to the top of the frame.

The above-described operation of the scanner is carried out when the dimensions of the part of the surface of the work scanned is such that the sweep across the whole frame 51 is required to scan it. When smaller surfaces are scanned position-adjustable limit switches may be provided or the block 75 may be provided with extended adjustable dogs which activate the limit switches when the block has swept through the desired distance.

The holographic echo-processing subassembly 29 (FIG. 1) includes, in addition to the gate 107, the holographic signal processing unit 91, a power amplifier 121, a transmit-receive switch 123 and a receiver amplifier 125. Where separate transducers are provided for transmitting and receiving the T-R switch 123 may be dispensed with. The holographic signal processing unit 91 includes the oscillator which supplies the waves for exciting the acoustic-lens transducer and facilities for mixing the received acoustic signal with an electrical analog of a reference acoustical wave. The unit 91 also includes the pulses for pulse modulating the waves from the oscillator to be transmitted by transducer 35, and the sample hold for echoes received. The oscillator which modulates the transmitted pulses also supplies the electrical analog of the acoustical reference wave which is mixed with the received signal to produce the hologram. When the gate 107 is open during the movement of the block 75 and the transducer subassembly 25 to the right, the holographic signal processing unit 91, through conductors 127 and 129 and the gate 107, actuates the power amplifier 121 to transmit pulses through the T-R switch 123 to energize the acoustic-lens transducer 35. The transducer 35 transmits acoustic energy which is focused at points 43 along the scanning contour of the transducer 35. This energy spreads through the work W producing echoes at the flaw 23 which are received by transducer 35, transmitted through the T-R switch 123 and the receiver amplifier 125 to the holographic signal processing unit 91. In the processing unit 91 the received signal is mixed with the electrical analog of the acoustical reference wave, phased in accordance with the instantaneous position of the transducer 35 during the scanning. The resultant signal is transmitted to the hologram unit 131 to produce an interference pattern on a film. During the scan, gate 111 is closed and focused-arc transducer transmits no acoustic energy and can transmit no echoes to echo-ranging unit 33.

The hologram unit 131 (FIG. 6) includes a light source 133, a camera 135 and a flexible light pipe 137. The camera 135 is firmly suspended by braces 139 from the scanner 27. The light source 133 is mounted in fixed position on the scanner. The light pipe extends from the source 133 to a position in the focal plane of the camera 135. In this position the end 145 of the light pipe 137 is secured to the bar 76 so that it too is moved by the block 75 as the block carries out the scanning operation. A flexible light-tight bellows 147 extends from the camera 135 to the bar 76 enclosing the source 145.

The acoustic energy of the echo is transmitted from the transducer 35, through conductor 141 and the T-R switch 123 to a preamplifier 143 (part of the receiver amplifier 125) mounted on the scanner 27, and thence to the holographic signal processing unit 91. Each echo signal received is maintained by a sample hold in the holographic signal processing unit 91 until the next echo is received. The light source 133 is energized from the output of the sample hold in the holographic signal processing unit 91. Its intensity is modulated in accordance with the received echo as reacted with the reference wave received from the scan-control logic 34 (scan control logic electronics 98). The light pipe 137 carries the modulated light from the source 133 to the focal plane of the camera 135 where it is photographed by the camera 135. The camera produces a hologram on a film. This hologram is an interference pattern which is later reconstructed in the reconstructor 150 (FIG. 1) by being illuminated by a laser beam. Typically, the laser beam is produced by a helium-neon laser.

The echo-ranging subassembly 33 (FIG. 1) includes, in addition to the gate 111, a pulser 151 for producing pulses to energize for focused-arc transducer 37, another transmit-receive switch 153, which may also be dispensed with if separate sensors 41 are used, for transmitting and receiving, and a receiver-amplifier 155. In addition, there is a display control 157, a display 159, typically a cathode-ray tube, and a storage device 161 for storing the received intelligence for later display. When the gate 111 is open, the pulses are impressed on the focused-arc transducer 37 through the T-R switch 153 producing acoustic energy focused and propagated along lines 45 as the transducer 37 scans the work 31. The echoes are transmitted through the T-R switch 153 to the receiver-amplifier 155 whence they are transmitted to the control 157 and the storage device 161. The display control 157 also receives synchronizing signals from the scan-control logic 34. The echo signals are impressed, typically on the grid of the cathode of the cathode-ray tube, to modulate the cathode ray beam. Scanning signals are impressed by the display control 157 between the plates 161 and 163 and 165 and 167 to produce scanning sweeps of the cathode ray tube in synchronism with the scan of scanner 27.

FIG. 7 shows diagrammatically the display on a cathode-ray tube 159 and the manner in which it is produced. A slice 171 through the work 31 is subjected to observation. The sketch 170 below the work W shows the orientation of the pattern produced by the acoustic energy. The beam intensity of the cathode-ray tube 159 is varied in accordance with the received echo.

It is asssummed that the horizontal deflection plates of FIG. 7 correspond to the plates 161 and 163 of FIG. 1 and the vertical deflection plates to the plates 165 and 167 of FIG. 1. The sweep between the plates 165 and 167 is produced by a variable-voltage supply 173, shown symbolically as a battery 175 and a voltage divider 177. The variation is in synchronism with the vertical scanning (as viewed in FIG. 7) of the slice 171 and is produced by a linkage 179 between the focused-arc transducer 37 and the wiper of the voltage divider 173. Signals are received only during the forward sweep (right to left of scanner 27) of the electron beam. During the return sweep transmission and signals are blocked by gate 111. The sweep between the plates 161 and 163 is produced by an X-axis sweep unit 181 controlled from a rate generator 183 synchronized with the corresponding scanning of the scanner which happens to be vertical as viewed in FIG. 2. The vertical scanning (as viewed from FIG. 7) and the sweep between plates 165 and 167 is at a high rate and the horizontal scanning on the sweep between the plates 161 and 163 at a low rate. The electron beam as it sweeps vertically is deflected only a small distance horizontally during each vertical sweep. FIG. 7 shows the pattern which is produced. The work W was a clad block of steel. The gray strip 191 on the left corresponds to the boundary between the cladding and the water. The wide white strip 193 to the right of the gray strip 191 corresponds to the cladding. The large gray area 195 corresponds to the steel. The white areas 197 within the area 195 correspond to the flaws. The narrow white strip 199 on the right of the area 195 corresponds to the boundary between the steel and the base of the vessel where this work W is disposed.

Figure 8:
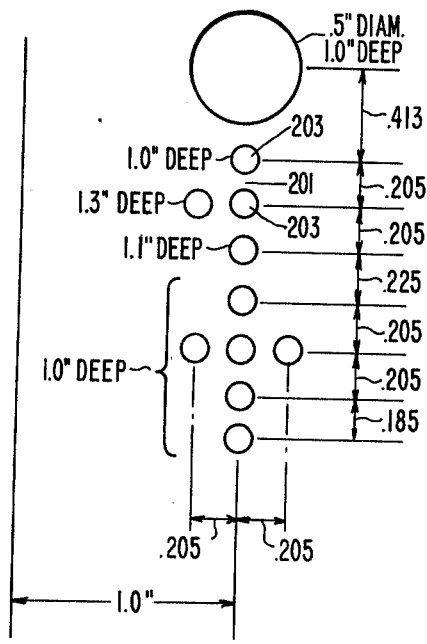
FIG. 8 is a diagrammatic view of the hole pattern of a specimen used in the practice of this invention.
Figure 6:
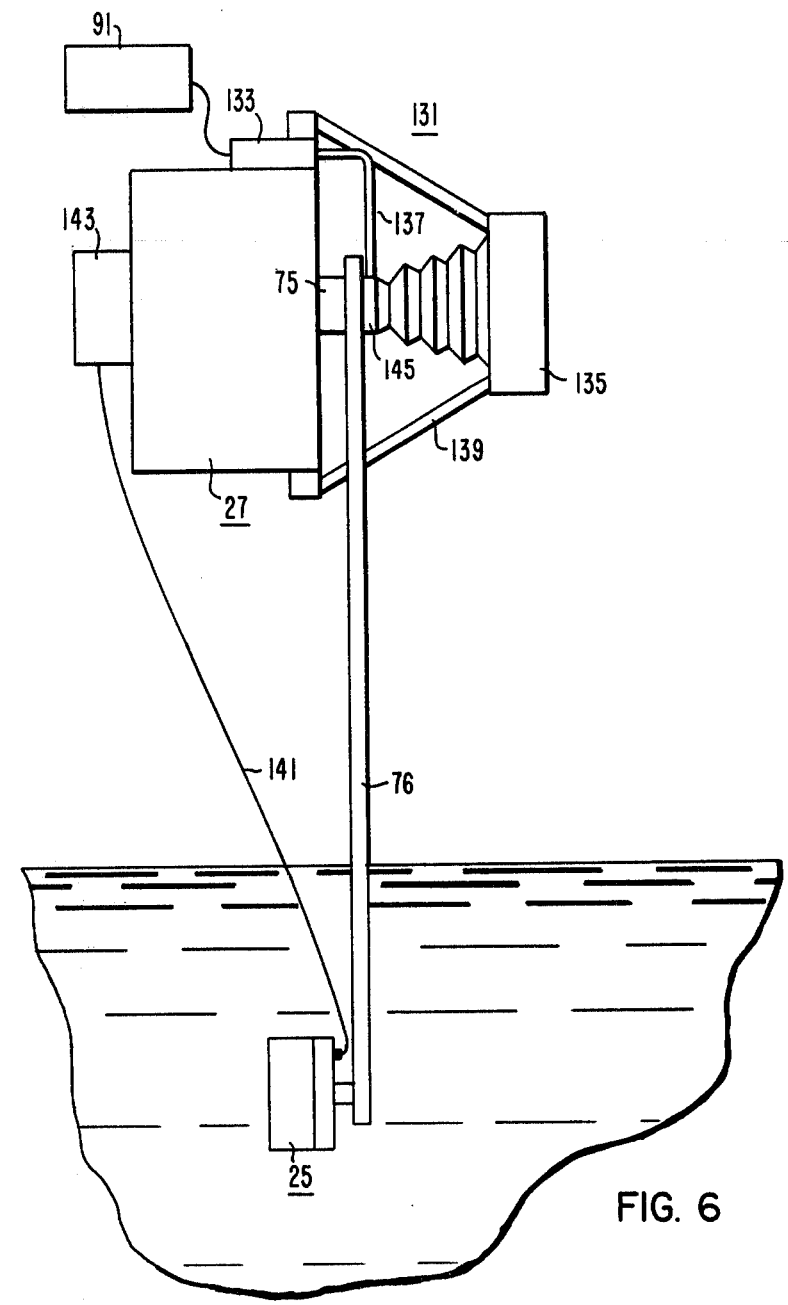
FIG. 6 is a view in side elevation, generally diagrammatic, showing the subassembly of the apparatus shown in FIG. 1 in whose operation the hologram is produced in the practice of this invention and cooperative components.
Figure 9:
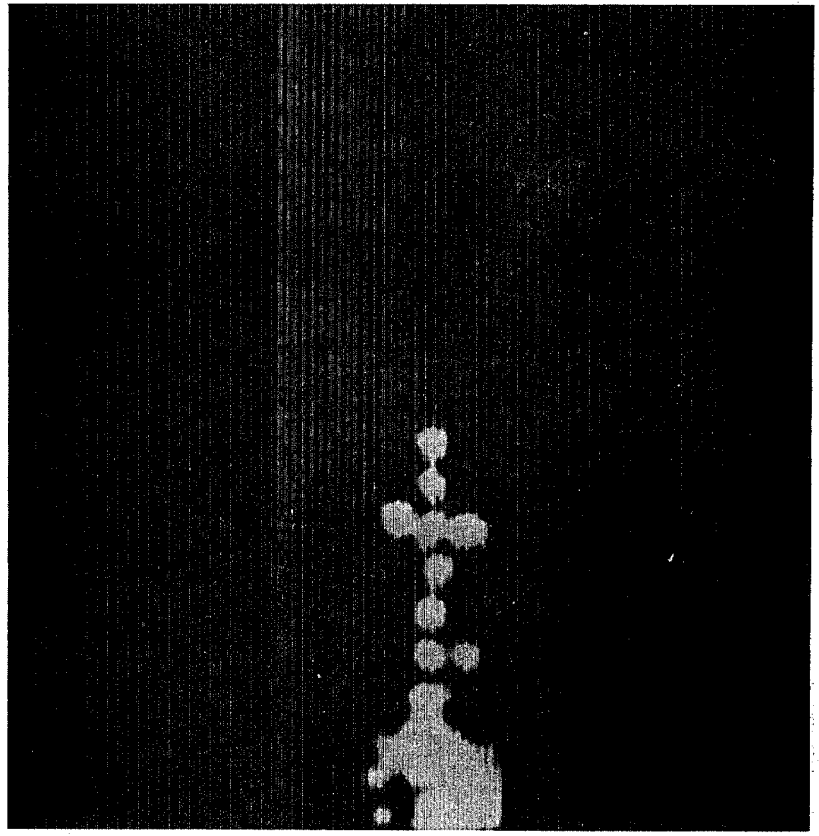
FIG. 9 is a photograph showing a C-scan image of the specimen shown in FIG. 8 produced with the focused-arc transducer.

FIG. 8 is a section through a test specimen W having a hole pattern simulating flaws. FIG. 9 is a photograph of a C-scan image produce for the specimen W shown in FIG. 8 with the focused-arc transducer 37. The acoustic energy was projected on a surface 31 parallel to the plane of FIG. 8 through the hole pattern. It is emphasized that the walls 201 of 0.08 inch between the holes 203 are resolved.

Figure 10:
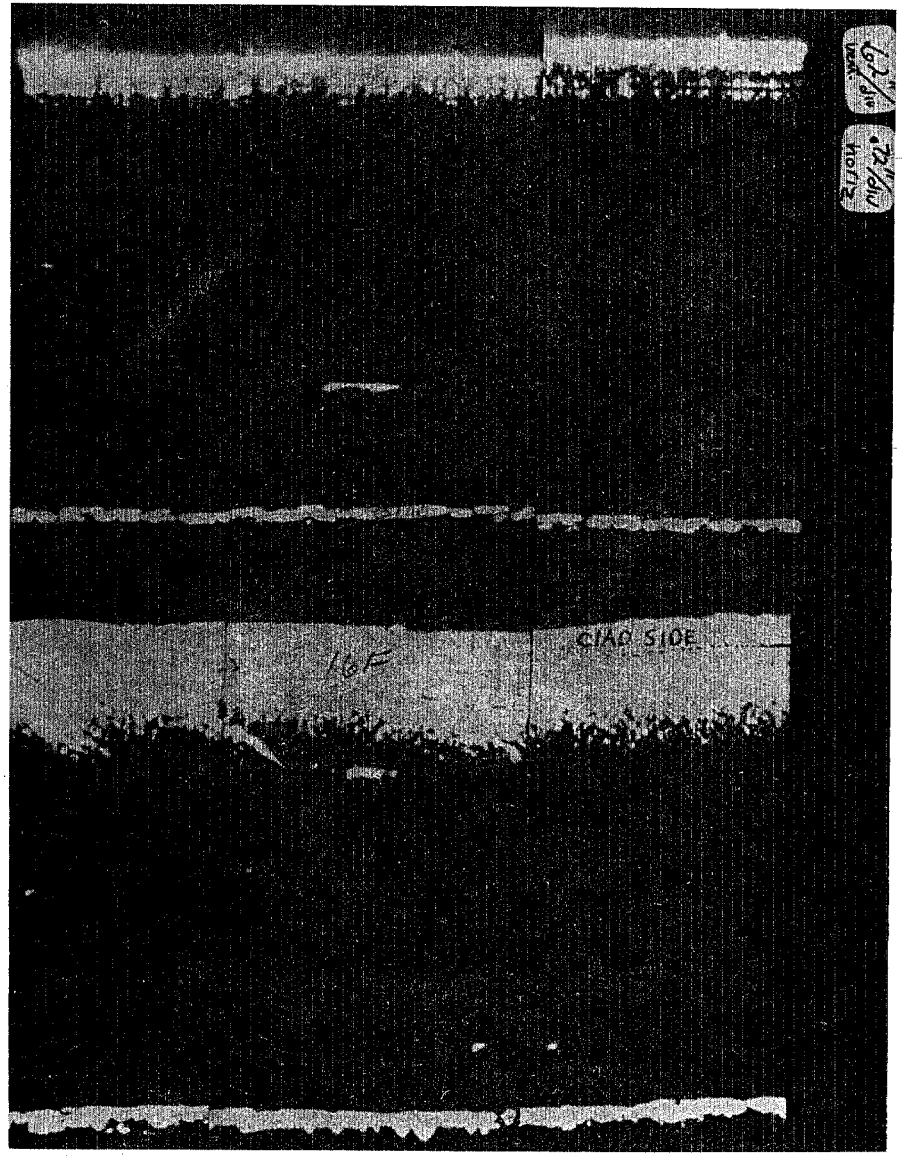
FIG. 10 is a photograph showing B-scan images of a clad specimen produced with a focused-arc transducer whose acoustic energy is propagated respectively, (a) on the clad face and (b) on the opposite unclad face of the specimen.

FIG. 10 shows a representative set of matching B-scan images of a weld specimen from a clad pressurized vessel of a nuclear reactor inspected with a focused-arc transducer. Photograph A shows the image produced with the acoustic energy projected on the cladding from the right to left as viewed in FIG. 10. The broad gray band 204 corresponds to the cladding. Photograph B shows the image produced with the acoustic energy projected on the unclad surface from left to right. FIG. 10 shows one of a number of sets of B-scan images produced with the specimen at 0.1 inch intervals; i.e., of slices of the specimen taken at intervals of 0.1 inch.

With the acoustic-lens transducer 35 and the holographic echo-processing subassembly, C-scan images corresponding to different depths of the work may be brought into focus by adjustment of the reconstruction. The reconstructed holograms may also be displayed on a cathode-ray tube. The cathode-ray tube may be remote from the scanner 27 simplifying scanner installation and handling.

Figure 11:
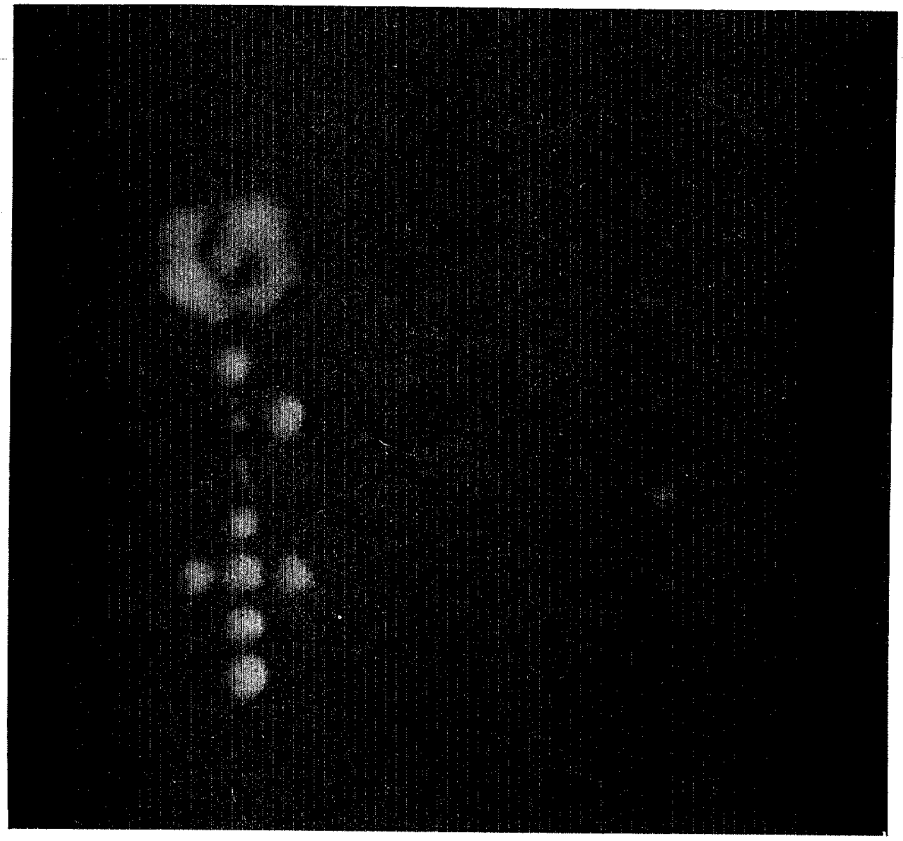
FIG. 11 is a photograph of a reconstructed hologram of a part of a nuclear-reactor vessel wall in which a hole pattern has been drilled for test purposes.

FIG. 11 shows a reconstruction of a hologram made with the acoustic-lens transducer of a test specimen having a series of ⅛ inch diameter flat bottom holes of approximately 0.2 inch centers through 4 inches of steel from a reactor vessel nozzle cutout. This pattern is similar to the pattern shown in FIG. 8. Also on the same reconstructed hologram are images of a series of ¼ inch diameter flat bottom holes, inclined 45° from the surface of the specimen. These images show excellent promise for accurate flaw definition. The images were produced with acoustic energy projected on the unclad side of the specimen. Attenuation of the energy by the stainless-steel cladding prevented obtaining good holograms from the clad side. The transducer 35 power output can be increased to overcome that problem.

In this invention the scanning with acoustic energy focused at a point 43 on or near the surface of the work W and holographic presentation is integrated with scanning with acoustic energy focused along a line 45 penetrating into the work and CRT or stored presentation. These modes of scanning and presentation mutually dovetail into each other, each being complementary to the other. The relationship is as follows:

1. The imaging by acoustic-lens transducer with its holographic presentation typically has a scanner and control which is superior to that of the focused-arc imaging and this scanner and control is adapted for use on the line-mode, focused-arc imaging by sharing of scanning sweep cycles.

2. Because the imaging by acoustic-lens transducer is carried out only in one direction of movement of the scanner 27, the backlash error, which would be introduced into the holographic presentation by opposite backlash settings when scanning in both directions, is eliminated without any loss in presentation.

3. The line-mode imaging with the focused arc-transducer has a narrow acoustic beam and it is difficult to find a detect or flaw for scan set-up. The acoustic-lens transducer halographic imaging with its wide divergent beam serves as a finder for the focused-line imaging.

4. The focused-arc transducer forms a family of parallel B-scan images; the acoustic-lens transducer imaging produces C-scan images which are at right angles to the B-scan images. A more complete view of the flaws is produced than with imaging of one mode or the other alone.

5. The acoustic-lens transducer imaging with its holographic presentation has superior resolution while the line-mode imaging has better penetration into the work.

6. With the acoustic-lens transducer coaxial with the focused-arc transducer the comparison of images is facilitated.

While a preferred embodiment of this invention has been disclosed, many modifications thereof are feasible. This invention should not be limited except insofar as is necessitated by the spirit of the prior art.

I claim:

1. Apparatus for detecting, characterizing and studying flaws in work by acoustical echo processing, said apparatus including first means for propagating acoustic energy on said work to produce a first echo from flaws in said work, and said first propagating means including first focusing means for focusing said first acoustic energy, second means for propagating second acoustic energy on said work to produce a second echo from flaws in said work, said second propagating means including second focusing means for focusing said acoustic energy, means, common to said first and second propagating means, for causing said first and second acoustic energy to scan said work, third means, connected to said scanning means and to said first and second propagating means, for producing a first echo indication only from the acoustic energy propagated by said first propagating means during a first part of each cycle of said scanning, and fourth means, connected to said scanning means and to said first and second propagating means, for producing only a second echo indication separate from said first echo indication during another part of each scanning cycle from the acoustic energy propagated by said second propagating means, said first focusing means being adapted to focus the first acoustic energy at a point on a plane at or near the work, said plane being generally perpendicular to the direction of propagation of the wave front of said first acoustic energy, and said second focusing means being adapted to focus the second acoustic energy, at each point along a line along the direction of the propagation of the wave front of said second acoustic energy.

2. The apparatus of claim 1 wherein the first propagating means includes a point-focussing transducer and the second propagating means includes a focused-arc transducer.

3. The apparatus of claim 1 wherein the first echo indication is a holographic display and the second echo indication is a cathode-ray tube display.

4. The apparatus of claim 2 wherein the point-focussing transducer and the focused-arc transducer are mounted so that the first and second acoustical energy are projected coaxially.

5. The apparatus of claim 1 wherein the first echo indication is a holographic display and the second echo indication is a storage pattern produced by storing the echoes in storage means.

6. The apparatus of claim 2 wherein the scanning means includes means, common to the point-focussing transducer and to the focused-arc transducer, for suspending said transducers, said acoustic-lens transducer being mounted centrally on said suspending means and said focused-arc transducer encircling said acoustic-lens transducer.

7. The apparatus of claim 1 wherein the first part of the scanning cycle is the part during which the scanning takes place in one direction and the other part of the scanning cycle is the part during which the scanning takes place in the opposite direction.

8. Apparatus for detecting, characterizing and studying flaws in work by echo ranging, said apparatus including first means for propagating acoustic energy on work to produce a first echo from said flaws in said work, said first means including a point-focussing transducer for focusing said acoustic energy at a point on or near a surface of said work, second means for propagating acoustic energy on work to produce a second echo from said flaws in said work, said second means including a focused-arc transducer for focusing said acoustic energy as it progresses into said work along a line penetrating into said work, means, common to said first and second propagating means, for causing the focused-acoustic energy from said acoustic-lens transducer and from said focused-arc transducer to scan said work together, said scanning means including means for sweeping said point-focussing transducer and said focused-arc transducer alternately in one direction and in the opposite direction across said work, and means for suppressing the propagation of acoustic energy by said first propagating means and also said first echo during the sweep in one direction and for suppressing the propagation of acoustic energy by said second propagating means and also said second echo during the sweep in said opposite direction.

* * * * *